United States Patent
Marchitto et al.

(10) Patent No.: US 8,343,606 B2
(45) Date of Patent: *Jan. 1, 2013

(54) ADHESIVE LAMINATES FOR RAPID WOUND OCCLUSION

(76) Inventors: Kevin S. Marchitto, Golden, CO (US); Stephen T. Flock, Arvada, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 13/291,619

(22) Filed: Nov. 8, 2011

(65) Prior Publication Data

US 2012/0052111 A1  Mar. 1, 2012

Related U.S. Application Data

(62) Division of application No. 12/804,292, filed on Jul. 19, 2010, now Pat. No. 8,053,052.

(51) Int. Cl.
  *B32B 9/00* (2006.01)
  *B32B 33/00* (2006.01)
  *B32B 3/10* (2006.01)
(52) U.S. Cl. ............ 428/40.1; 428/40.2; 428/40.5; 428/40.6; 428/41.7; 428/131

(58) Field of Classification Search ............ 428/40.1, 428/40.2, 40.5, 40.6, 41.7, 131
See application file for complete search history.

(56) References Cited

U.S. PATENT DOCUMENTS

| | | | |
|---|---|---|---|
| 4,427,737 A | 1/1984 | Cilento |
| 4,447,482 A | 5/1984 | Heinzelman |
| 4,538,603 A | 9/1985 | Pawelchak |
| 5,681,579 A | 10/1997 | Freeman |
| 5,700,478 A | 12/1997 | Biegajski |
| 5,770,229 A | 6/1998 | Tanihara |
| 6,261,593 B1 | 7/2001 | Muchin |
| 6,335,388 B1 | 1/2002 | Fotinos |
| 6,632,450 B1 | 10/2003 | Gregory |
| 2002/0049503 A1 | 4/2002 | Milbocker |
| 2002/0148556 A1 | 10/2002 | Kawada |
| 2003/0080151 A1 | 5/2003 | D'Alessio |

FOREIGN PATENT DOCUMENTS

| | | |
|---|---|---|
| FR | WO91/01688 A1 | 2/1991 |
| US | WO03/008003 A1 | 1/2003 |

*Primary Examiner* — Victor Chang
(74) *Attorney, Agent, or Firm* — Benjamin Aaron Adler

(57) ABSTRACT

Provided herein are protective laminate devices comprising a biocompatible non-adherent substance and a fast-setting adhesive and methods of use. Also provided is a dispenser for an adhesive tape. The protective laminate devices and methods may be used for wound closure.

25 Claims, 5 Drawing Sheets

ADHESIVE LAMINATES FOR RAPID WOUND OCCLUSION

CROSS-REFERENCE TO RELATED APPLICATIONS

This divisional application claims benefit of priority under 35 U.S.C. §120 of pending continuation application U.S. Ser. No. 12/804,292, filed Jul. 19, 2010, now U.S. Pat. No. 8,053,052, which claims benefit of priority under 35 U.S.C. §120 of non-provisional application U.S. Ser. No. 11/032,427, filed Jan. 10, 2005, now U.S. Pat. No. 7,758,939, which claims benefit of priority under 35 U.S.C. §119(e) of provisional application U.S. Ser. No. 60/534,917, filed Jan. 8, 2004, now abandoned, then entirety of all of which are hereby incorporated by reference.

BACKGROUND OF THE INVENTION

1. Field of the Invention

The present invention relates generally to the fields of biomedical engineering, biochemistry and surgical procedures. More specifically, the present invention provides a device and methods using wound laminates and occlusive coatings suitable for sealing tissues or enhancing wound healing.

2. Description of the Related Art

Conventional methods of wound closure following surgery consist of applying sutures or staples to join two or more tissues that have been dissected. Various alternative methods have been developed to fasten tissues together without the use of a conventional staple or suture. Commercial electrosurgery and electrocautery devices, which employ heat, are often used for sealing external and internal wounds. Other ways for sealing vessels using other forms of electromagnetic energy, such as that produced by lasers, are known.

Tissue adhesives consisting of biomolecules, such as fibrin, currently are used to "glue" tissue-to-tissue. The results are often sub-optimal due to weak adherence and dissolution of the fibrin clot. Cyanoacrylates of various types, derived from instant bonding glues, e.g., SUPERGLUE™, also are used on tissue and available for use in the home, although currently they are approved only in the United States for external use. DERMABOND™, an approved topical skin adhesive, is 2-octyl cyanoacrylate with added colorant D&C Violet #2 for easy visualization. The package insert for this material warns that any inadvertent contact with any body tissue and any surfaces or equipment, such as latex gloves or stainless steel, should be avoided. The adhesive is applied by apposing the tissue edges with fingers or forceps and applying the liquid adhesive in several stroking motions not unlike that used with a paintbrush, allowing time to dry in between strokes.

Practically, there is a significant problem with the use of fast-setting skin adhesives. Bonding may result in unintentional bonding of human or inanimate applicators. During application of cyanoacrylate-based adhesives the care provider often glues his or her examination gloves to the patients. Unintentional bonding requires the bonded materials to be peeled apart potentially causing local trauma. Acetone is a solvent of cyanoacrylate that can help loosen the bond, but the use of acetone on an open wound can be problematic. Furthermore, DERMABOND™ is not indicated for use in high-tension skin areas, where it's holding force may be insufficient to maintain wound closure, or near the eyes where runoff of the glue may result in unintentional adhesion.

The inventors have recognized a need in the art for an improvement in the devices and methods used for joining tissues separated through surgery or through trauma. The prior art is deficient in the lack of fast-setting adhesives and the use thereof in minimizing the risk of unintentional bonding during use of these fast-setting adhesives. The present invention fulfills this longstanding need and desire in the art.

SUMMARY OF THE INVENTION

The present invention is directed to a laminate device for protecting an adhesive during manipulation thereof. The laminate device comprises an adhesive and at least one layer of a biocompatible non-adherent substance disposed in protective relationship to the adhesive. The present invention is directed to a device further comprising at least one removable layer disposed in contact with the adhesive, with one or more layers of the biocompatible non-adherent substance or a combination thereof. The present invention also is directed further to a device comprising an emulsifying agent, a solubilizing agent, a wetting agent, a taste modifying agent, a plasticizer, a bioactive agent, a water soluble inert filler, a preservative, a buffering agent, a coloring agent, a stabilizer, or a combination thereof and/or a pharmaceutical in one or more biocompatible non-adherent layers.

The present invention also is directed to a method of preventing unintentional bonding of an adhesive during application thereof to one or more tissues. The laminate device described herein is positioned on the tissue(s) such that the adhesive layer comprising the laminate device is in contact with the tissue(s) and activating the adhesive. The removal of the removable layer(s) comprising the laminate device is dependent upon the disposition of the removable layer within the laminate device. If the removable layer is disposed only on a surface of the adhesive layer, the removable layer is removed prior to positioning the laminate device. If the removable layer(s) is disposed on one or more layers of the biocompatible non-adherent substance comprising the laminate device, the removable layer(s) is removed after activating the adhesive or a combination thereof. The biocompatible non-adherent substance and the removable layer(s) protect the adhesive layer during application thereof thereby preventing unintentional bonding of the adhesive. The method further may comprise setting the adhesive to join the tissues.

The present invention is directed further to a method of delivering a bioactive agent to one or more tissues. The laminate device described herein is positioned upon the tissue(s) where one or more of the layers of the laminate device comprises the bioactive agent thereby delivering the bioactive agent to the tissue(s). The present invention is directed further to a related method where the bioactive agent is the adhesive comprising the layer in contact with the tissue(s) whereby setting the adhesive joins the tissue(s). The present invention is directed further to another related method where the bioactive agent is a pharmaceutical comprising one or more of the layers of the laminate device described herein disposed in protective relationship with a porous or permeable adhesive layer in contact with the tissue(s) whereby the pharmaceutical diffuses therefrom through the porous or permeable adhesive layer.

The present invention is directed further still to a dispenser for an adhesive tape. The dispenser comprises a biocompatible non-adherent substance, a means to dispense an adhesive layer onto a layer of the biocompatible non-adherent substance, a means to cut the combined layers, and a housing having an opening.

The present invention is directed further still to a method of forming an adhesive tape to join one or more tissues. A length of the layer of the biocompatible non-adherent substance is withdrawn through the opening in the dispenser described immediately supra while simultaneously dispensing the adhesive layer along the length of the layer of the biocompatible non-adherent substance via the brush in the dispensor. The combined layers are cut via the cutting means comprising the dispenser after sufficient length has been withdrawn thereby forming the adhesive tape. Additionally, the method provides for positioning the adhesive tape on one or more tissues such that the adhesive layer is in contact with the tissue(s) and setting the adhesive thereby joining the tissue(s).

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
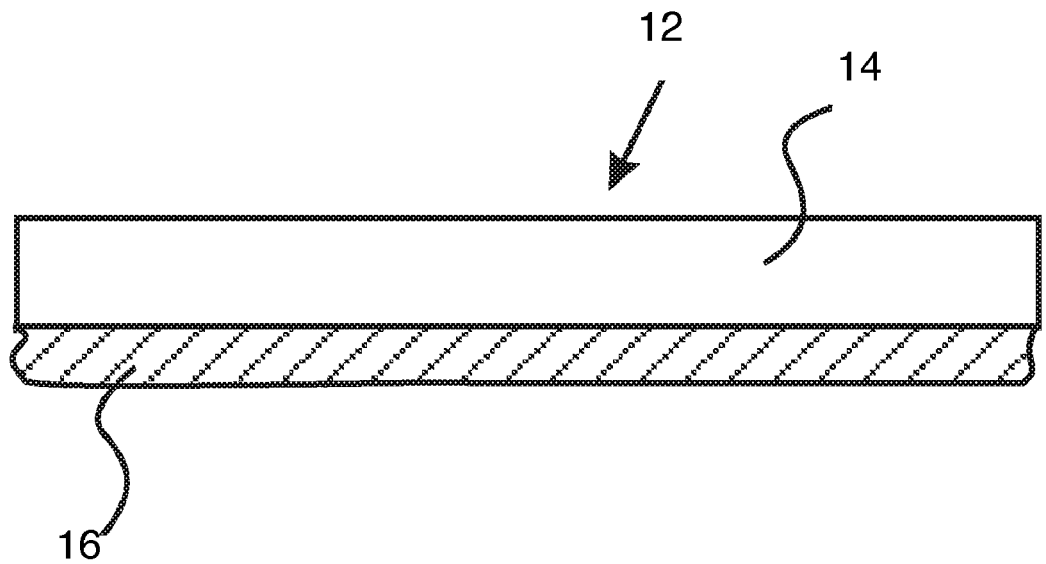
FIGS. 1A-1C depict an adherent tissue patch without a non-stick removable layer (FIG. 1A) and with a non-stick removable layer (FIGS. 1B-1C).

In one embodiment of the present there is provided a laminate device for protecting an adhesive during manipulation thereof, comprising the adhesive; and at least one layer of a biocompatible non-adherent substance disposed in protective relationship to the adhesive. In this embodiment the laminate device may comprise a patch.

Further to this embodiment the laminate device may comprise at least one removable layer disposed in contact with the adhesive, with one or more layers of the biocompatible non-adherent substance or a combination thereof. In one aspect of this embodiment the removable layer is disposed in contact with the adhesive and is removable prior to manipulation of the adhesive. In another aspect the removable layer is disposed between the adhesive and the biocompatible non-adherent substance and is removable after manipulation of the adhesive. In yet another aspect the removable layer is disposed in a covering relationship to an outer layer of the biocompatible non-adherent substance and is removable after manipulation of the adhesive. The removable layer may comprise teflon or a cellulose impregnated with a lipid. Examples of the lipid are lecithin, polyethylene glycol or a wax.

In all aspects of this embodiment the biocompatible non-adherent substance dissolves upon contact with a fluid, e.g., water. The biocompatible non-adherent substance may be a hydrocolloid such as pullulan. Additionally, in all aspects of this embodiment the adhesive may comprise a cyanoacrylate or a derivative thereof, a protein or a synthetic polymer. Furthermore the adhesive may be porous or permeable.

In one aspect of this embodiment the biocompatible non-adherent substance may be disposed on a surface of the adhesive. In another aspect one or more layer(s) of the biocompatible non-adherent substance may comprise the adhesive incorporated therein. In a related aspect the adhesive may be contained within a rupturable reservoir within one of the layer(s).

In related aspects one or more layers of the biocompatible non-adherent substance further may comprise an emulsifying agent, a solubilizing agent, a wetting agent, a taste modifying agent, a plasticizer, an active agent, a water soluble inert filler, a preservative, a buffering agent, a coloring agent, an aesthetic design, a stabilizer, or a combination thereof. In another related aspect one or more layers of the biocompatible non-adherent substance further comprises a pharmaceutical. In yet another related aspect the pharmaceutical may be contained within a rupturable reservoir within the layer(s).

In another embodiment of the present invention, there is provided a method of preventing unintentional bonding of an adhesive during application thereof to one or more tissues, comprising positioning the laminate device described herein onto the tissue(s) where the adhesive layer comprising the laminate device is in contact with the tissue(s); activating the adhesive; and removing the removable layer(s) comprising the laminate device, where, if the removable layer is disposed only on a surface of the adhesive layer, then removable layer is removed prior to positioning said laminate device or if the removable layer(s) is disposed on one or more layers of the biocompatible non-adherent substance comprising the laminate device, then the removable layer(s) is removed after activating the adhesive or a combination thereof; wherein the biocompatible non-adherent substance and the removable layer(s) protect the adhesive layer during application thereof thereby preventing unintentional bonding of the adhesive.

Further to this embodiment the method comprises setting the adhesive to join the tissue(s). In this embodiment the layers of the biocompatible non-adherent substance and the additional agents added thereto, the adhesive layer, the removable layers and the disposition of the layers within the laminate device are as described supra. Additionally, the biocompatible non-adherent substances and the adhesives are as described supra.

In yet another embodiment of the present invention, there is provided a method of delivering a bioactive agent to one or more tissues, comprising positioning the laminate device described herein in contact with said tissue(s) wherein one or more of the layers of the laminate device comprises said bioactive agent thereby delivering said bioactive agent to the tissue(s).

In an aspect of this embodiment the bioactive agent is an adhesive comprising the layer in contact with the tissue(s). The method further comprises setting the adhesive to join the tissues. In a related aspect the adhesive may be contained within a rupturable reservoir. The method further comprises rupturing the reservoir prior to setting the adhesive.

In another aspect of this embodiment the bioactive agent is a pharmaceutical comprising one or more of the layers disposed in protective relationship with a porous or permeable adhesive in contact with the tissue(s). The method further comprises diffusing the pharmaceutical from the layer(s) through the porous or permeable adhesive layer. In a related aspect the pharmaceutical may be contained within a rupturable reservoir. The method further comprises rupturing the reservoir prior to diffusing the adhesive. In all aspects of this embodiment the laminate device and the adhesive are as described supra.

In still another embodiment of the present invention, there is provided a dispenser for an adhesive tape, comprising a biocompatible non-adherent substance; a means to dispense an adhesive layer onto a layer of the biocompatible non-adherent substance; a means to cut the combined layers; and a housing having an opening. The biocompatible non-adherent substance, the layer thereof and the additional agents added thereto and the adhesive are as described supra.

In one aspect of this embodiment the means to dispense the adhesive comprises a brush impregnated with the adhesive. In a related aspect the means to dispense the adhesive comprises a brush and an ampoule to contain the adhesive fluidly connected to the brush.

In still another embodiment of the present invention, there is provided a method of forming an adhesive tape to join one or more tissues, comprising withdrawing a length of the layer of the biocompatible non-adherent substance through the opening in the dispenser described supra; simultaneously dispensing the adhesive layer along the length of the layer of the biocompatible non-adherent substance via the brush in the dispenser and cutting the combined layers via the cutting means comprising the dispenser after sufficient length has been withdrawn thereby forming the adhesive tape. Further to this embodiment the method provides for positioning the adhesive tape on one or more tissues such that the adhesive layer is in contact with the tissue(s) and setting the adhesive thereby joining the tissue(s).

Provided herein are protective adherent devices, patches or adhesive tapes to join and aid the joining of biological tissues by adhesion. The patch or tape includes a fast-setting adhesive or other type of tissue adhesive and a shield or laminate(s) that are at least in part comprised of a protective layer(s) that preferentially dissolve upon exposure to body fluids or water. Additional layers of the patch may include pharmaceuticals or other biologics. Also provided is a device to dispense the tape comprising a biocompatible laminate and fast-setting adhesive. The protective patches or tapes and dispensors may be used for closing a wound following trauma or a surgical procedure.

A tissue patch may comprise a protective layer of a laminate or shield comprising a non-adherent biocompatible material placed in contact with a fast-setting adhesive layer. The adhesive is, preferably, a cyanoacrylate, or is derived from the cyanoacrylates, but also may include other synthetic and naturally-occurring adhesives used in tissues. Included are protein adhesives, e.g. fibrin, collagen, and activated adhesives, such as those used in laser tissue welding.

Optionally, the non-adherent biocompatible material may dissolve in water. The biocompatible material may be a hydrocolloid material and may comprise a carbohydrate, such as pullulan. The biocompatible material comprising the shield or laminate may be, inter alia, poly(DL-lactic-co-glycolic acid), whey-protein emulsion with sorbitol, glycerol with butterfat and candelilla wax, arabinoxylans and hydrogenated palm kernel oil, calcium caseinate and whey protein, carboxymethylcellulose, pectin, milk-protein, or resins. Alternatively, the biocompatible material may be coated with a non-stick material, such as, but not limited to, a lipid, on the surface that comes into contact with the adhesive and so can be immediately removed from the adhesive upon polymerization of the latter.

A non-dissolving biocompatible laminate or shield may be placed in contact with a fast-setting adhesive to form a tape. The non-dissolving biocompatible laminate is textured with a plurality of projections to aid in wound closure. The projections provide means to manually draw apposed tissue toward the dissection line without necessity of forceps.

Additionally, the laminate tissue patch may comprise a non-stick removable layer to prevent inadvertent adhesion to the adhesive. The non-stick removable layer may be positioned in contact with the dissolvable biocompatible laminate which is in contact with the fast-setting adhesive layer to form a tissue tape. Alternatively, the laminate tissue patch may comprise a dissolvable biocompatible material as an upper layer which is in contact with the fast-setting adhesive layer. The other side of the fast-setting adhesive is covered with the removable layer which prevents inadvertent sticking to the patch. The removable layer may be peeled away to expose the fast-setting adhesive prior to positioning the tissue patch on the individual.

The removable layer may comprise materials which do not stick to the fast-setting adhesive. For example, if the fast-setting adhesive is cyanoacrylate, the removable layer may comprise teflon or cellulose impregnated with a lipid, e.g. lecithin or wax. Representative lipids are lecithin or polyethylene glycol, and representative waxes are paraffin, beeswax, candelilla, carnauba, or ceresine.

The tissue patch may fasten at least two substrates in order to effect a bond between the substrates in an individual, in a plant or animal or in cells and tissues of other organisms. The patch is useful for approximating apposed edges of dissected tissue, for compromising infected tissue, for holding pharmaceuticals in place, or for occluding open wounds, iatrogenic or otherwise, for the purpose of minimizing the chance of infection. The biocompatible shield or laminate is intended to prevent the care-provider from inadvertently sticking him/herself to the adhesive material and yet will dissolve upon exposure to water without undesirable toxicity to the individual. Potentially corrosive, toxic, or otherwise undesirable material is shielded from contact with a human or inanimate applicator, thus allowing the applicator to manipulate the materials with greater freedom.

Generally, the protective layer or shield, either biocompatible or not, may comprise in part or in whole a hydrocolloid. Preferably, the hydrocolloid comprises a water soluble natural polysaccharide or derivatives, including pectin and derivatives, guar gum arabic, tragacanth gum, xanthan gum, gellan sodium salt, propyleneglycol alginate, starches (amylose, amylopectin), modified starches, hydroxyethyl starch, pullulan, carboxymethyl starch, gum ghatti, okra gum, karaya gum, dextrans, dextrins and maltodextrins, konjac, acemannan from aloe, locust bean gum, tara gum, quince seed gum, fenugreek seed gum, scleroglucan, gum arabic, psyllium seed gum, tamarind gum, oat gum, quince seed gum, carrageenans, scleraglucan, succinoglucan, larch arabinogalactan, flaxseed gum, chondroitin sulfates, hyaluronic acid, curdlan, chitosan, deacetylated konjac, and *rhizobium* gum.

The hydrocolloid may be a water soluble non-gelling polypeptide or protein exemplified by gelatins, albumins, milk proteins, soy protein, and whey proteins. The hydrocolloid further may be selected from a group of synthetic hydrocolloids exemplified by polyethyleneimine, hydroxyethyl cellulose, sodium carboxymethyl cellulose, carboxymethyl cellulose, hydroxypropyl cellulose, hydroxypropyl methyl cellulose, methyl cellulose, ethyl cellulose, polyacrylic acids, low molecular weight polyacrylamides and their sodium salts (carbomers), polyvinylpyrollidone, polyethylene glycols, polyethylene oxides, polyvinyl alcohols, pluronics, tetronics, and other block co-polymers, carboxyvinyl polymers, and colloidal silicon dioxide.

Suitable hydrocolloids or mixtures producing synergistic properties comprise natural seaweeds, natural seed gums, natural plant exudates, natural fruit extracts, biosynthetic gums, gelatines, biosynthetic processed starch or cellulosic materials, alginates, agar gum, guar gum, locust bean gum (carob), carrageenan, tara gum, gum arabic, ghatti gum, *Khaya grandifolia* gum, tragacanth gum, karaya gum, pectin, arabian (araban), xanthan, gellan, starch, Konjac mannan, galactomannan, funoran, are xanthan, acetan, gellan, welan, rhamsan, furcelleran, succinoglycan, scleroglycan, schizophyllan, tamarind gum, curdlan, pullulan, and dextran Additionally, the biocompatible laminate or shield may comprise any or all of emulsifying agents, solubilizing agents, wetting agents, taste modifying agents, plasticizers, active agents, water soluble inert fillers, preservatives, buffering agents, coloring agents, and stabilizers. Addition of a plasticizer to the formulation can improve flexibility. The plasticizer or mixture of plasticizers may be polyethylene glycol, glycerol, sorbitol, sucrose, corn syrup, fructose, dioctylsodiumsulfosuccinate, triethylcitrate, tributylcitrate, 1,2-propylenglycol, mono-, di- or triacetates of glycerol, or natural gums. Preferred plasticizers are glycerol, polyethylene glycol, propylene glycol, citrates and their combinations. The amount of plasticizer depends on the final application.

Examples of natural water-soluble polymers include plant-type polymers, microorganism-type polymers and animal-type polymers. A plant-type polymer may be gum arabic, gum tragacanth, galactan, guar gum, carob gum, karaya gum, carrageenan, pectin, agar, quince seed or *Cydonia oblonga*, algae colloids such as brown algae extract, starches such as rice, corn, potato, and wheat, and glycyrrhizic acid. Microorganism-type polymers may be xanthan gum, dextran, succinoglucan, and pullulan. Animal-type polymers may be collagen, casein, albumin, and gelatin.

Examples of the semisynthetic water-soluble polymers include starch-type polymers, cellulosic polymers and alginic acid-type polymers. Starch-type polymers may be carboxymethyl starch and methylhydroxypropyl starch. Cellulosic polymers may be methyl cellulose, ethyl cellulose, methylhydroxypropyl cellulose, hydroxyethyl cellulose, cellulose sodium sulfate, hydroxypropyl cellulose, carboxymethylcellulose, sodium carboxymethyl cellulose, crystal cellulose, and cellulose powder. Alginic acid-type polymers may be sodium alginate and\ propyleneglycol-alginate.

Examples of the synthetic water-soluble polymers include vinyl polymers, polyoxyethylene-type polymers, acrylic polymers, and cationic polymers, and polyethyleneimine. Vinyl polymers may be polyvinyl alcohol, polyvinyl methyl ether, polyvinylpyrrolidone, carboxy vinyl polymer. Polyoxyethylene-type polymers may be a copolymer of polyethylene glycol 20,000, 40,000, or 60,000 and polyoxyethylene polyoxypropylene. Acrylic polymers may be sodium polyacrylate, polyethylacrylate, and polyacrylamide.

Thickeners may include gum arabic, carrageenan, karaya gum, gum tragacanth, carob gum, quince seed or *Cydonia oblonga*, casein, dextrin, gelatin, sodium pectate, sodium alginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate or beagum, laponite, and silicic acid anhydride.

Additionally, the present invention provides a shield or laminate for an adhesive or an adhesive laminate whereby an external layer of the shield may dissolve upon contact with fluids. The soluble, external shield may serve as an applicator to facilitate the application of the adhesive to tissue. The shield or laminate also may comprise one or more internal layers, reservoirs or pooled materials containing the adhesive. Furthermore multiple layers or reservoirs may contain a biologic, a drug or other pharmaceutical substance, whereby the system becomes a drug delivery device. The bioactive material may be, although not limited to, one of or a combination of nitroglycerin, an anti-nauseant, an antibiotic, a hormone, a steroidal anti-inflammatory agent, a non-steroid antiinflammatory agent, a chemotherapeutic agent, an anti-cancer agent, an immunogen, an analgesic, an anti-viral agent or an anti-fungal agent.

The layers used as a barrier to separate the adhesive from the backing, or the adhesive from the substrate, may be removed upon application. Alternatively, a layer may be designed to allow for release of the active agent, e.g., adhesive or biologic, drug or other pharmaceutical substance, upon activation, whereby the activation consists of compromising the layer. Examples include perforation, or dissolution upon exposure to fluids or heat, e.g. body heat, thus allowing the active agent to flow past the barrier. Alternatively, the adhesive layer may be separate from the barrier layer and may be porous or permeable whereby, upon mechanically compromising the integrity of a reservoir contained within the barrier layer or laminate, a bioactive material, such as a pharmaceutical, is released to diffuse through the adhesive layer.

The present invention provides dispensers for the laminates and adhesives described herein. The dispenser may hold the laminate, a portion of which is withdrawn from the dispenser as needed. The fast-setting adhesive is applied to a side of the laminate whereupon the dispenser is used to cut the laminate. This provides an adhesive tape used to effect a bond between the substrates in an individual. Alternatively, a dispenser may dispense a fast-setting adhesive contiguous with the laminate. When the adhesive dispenser is mechanically disrupted, the adhesive flows into the laminate.

As described below, the invention provides a number of therapeutic advantages and uses, however such advantages and uses are not limited by such description. Embodiments of the present invention are better illustrated with reference to the FIGS. 1-5, however, such reference is not meant to limit the present invention in any fashion. The embodiments and variations described in detail herein are to be interpreted by the appended claims and equivalents thereof.

Figure 1B:
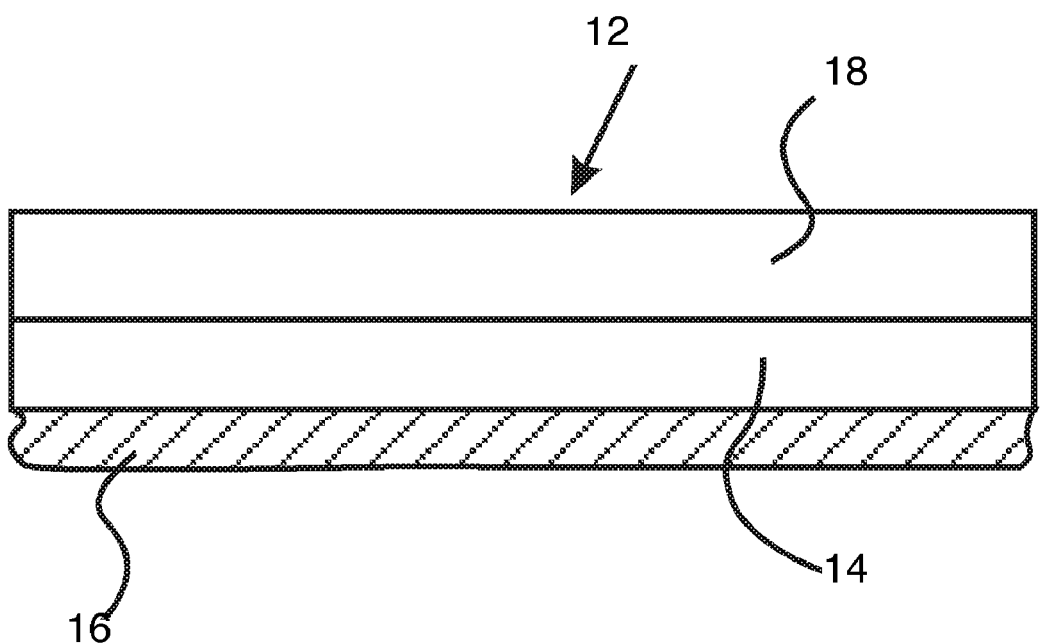
Figure 1C:
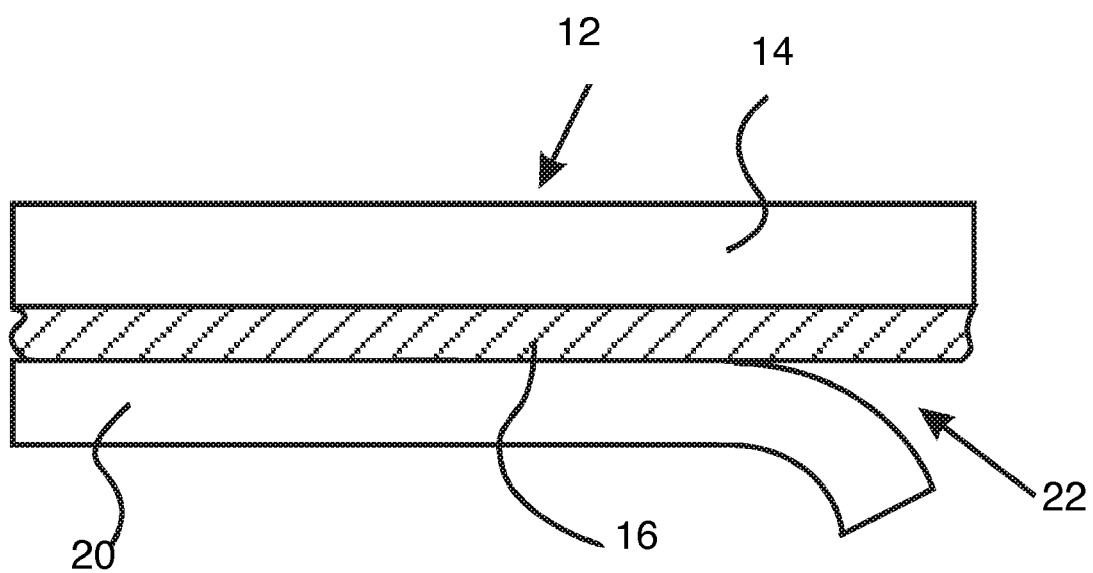

FIGS. 1A-1C depict examples of adherent tissue patches. In FIG. 1A the tissue patch 12 comprises a protective layer 14, which is a non-adherent biocompatible material and optionally water soluble, the inferior surface of which is disposed on and in contact with the superior surface of a fast-setting adhesive layer 16, such as cyanoacrylate. Alternatively, the biocompatible material 14 may be coated with a non-stick material (not shown), such as a lipid, on the inferior surface that comes into contact with the adhesive 16, and so can be immediately removed from the adhesive 16 upon polymerization of the latter.

FIG. 1B depicts a tissue patch 12 comprising a biocompatible material 14, the inferior surface of which is disposed on and in contact with the superior surface of a fast-setting adhesive layer 16. The superior surface of the biocompatible material 14 is disposed on and in contact with the inferior surface of a covering material 18 that allows the care provider to apply downward force to the patch 12 and not contaminate the biocompatible material 14. The covering material 18 may be peeled away from the biocompatible material 14 after application of the patch 12 to the tissue (not shown).

Alternatively, in FIG. 1C, a patch 12 comprises a biocompatible material 14, the inferior surface of which is disposed on and in contact with the superior surface of a fast-setting adhesive layer 16. The inferior side of the fast-setting adhesive 16 is in contact with and covered by a removable layer 20 intended to prevent inadvertent sticking to the patch 12. Peeling away the removable layer 20 at position 22 exposes the fast-setting adhesive 14 prior to positioning the patch 12 on the individual. The removable layer 20 may comprise materials which do not stick to the fast-setting adhesive 14.

Figure 2:
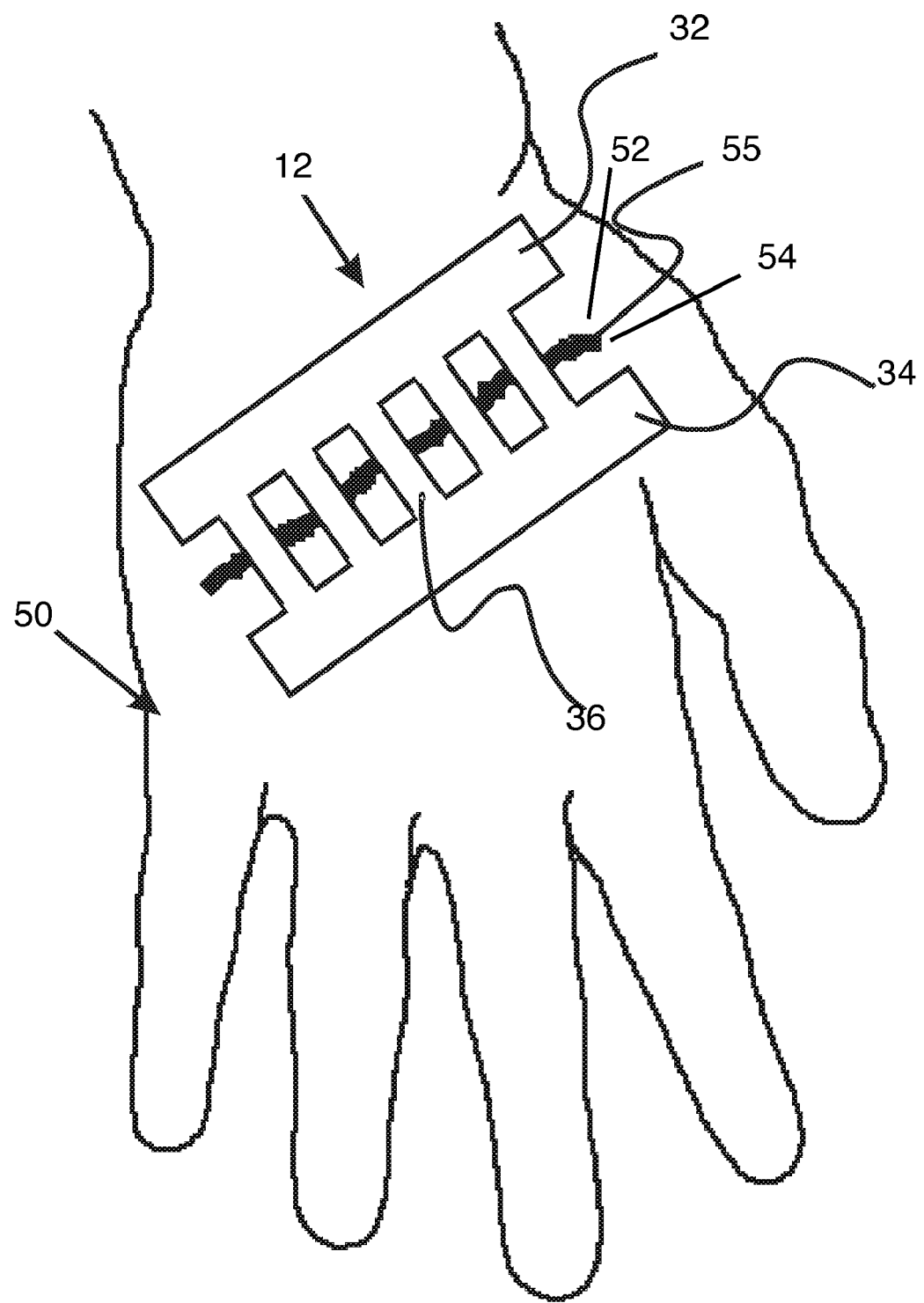
FIG. 2 depicts an adherent tissue patch positioned over a laceration on the dorsal aspect of a hand.
Figure 3A:
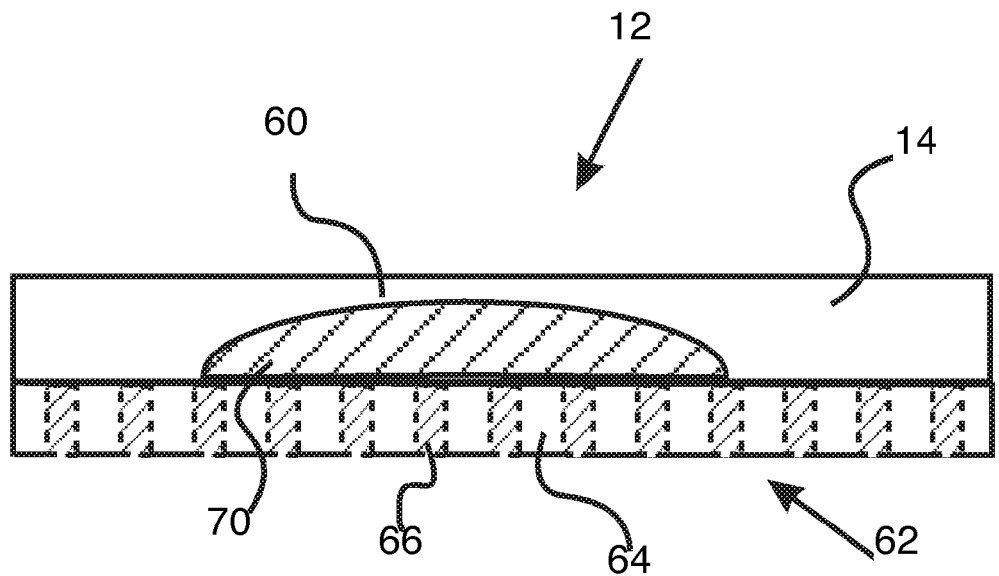
FIGS. 3A-3B depict an adhesive patch comprising a reservoir containing a bioactive material incorporated within the patch and a porous adhesive layer (FIG. 3A) or a permeable adhesive layer (FIG. 3B).

With continued reference to FIG. 1A, FIG. 2 depicts a laminate adhesive patch 12, which has a shape that allows application to the substrates, e.g., a hand 50 with wound 55, in a way that the apposed edges 52,54 of the wound 50 may be drawn together without the use of forceps or without inadvertent adhesion of the care-provider to the patch 12. A first part 32 of the patch 12 may be applied to the side of the wound 50 having wound edge 52. A second part 34 of the patch 12 may be applied to the side of the wound 50 having wound edge 54 to maintain close contact between the apposed wound edges 52,54. The patch 12 further comprises an additional plurality of parts 36 joining the first and second parts 32,34 of the patch 12 which maintain tension across the wound 50 thus minimizing dihescence. Optionally, parts 36 may shrink with the application of heat Still with continued reference to FIG. 1A, FIG. 3A depicts a laminate adhesive patch 12 comprising a biocompatible material 14, which has an internal reservoir 60 containing bioactive material 70, the inferior surface of which is disposed on and in contact with the superior surface of a porous biocompatible adhesive layer 62 comprising a fast-setting adhesive 64 and perforations 66 between the superior and inferior surfaces of the porous biocompatible layer 62. Upon mechanically compromising the integrity of the reservoir 60, the bioactive material 70 diffuses through the porous layer 62 and is beneficially delivered to the tissue (not shown) on which the patch 12 is applied.

Figure 3B:
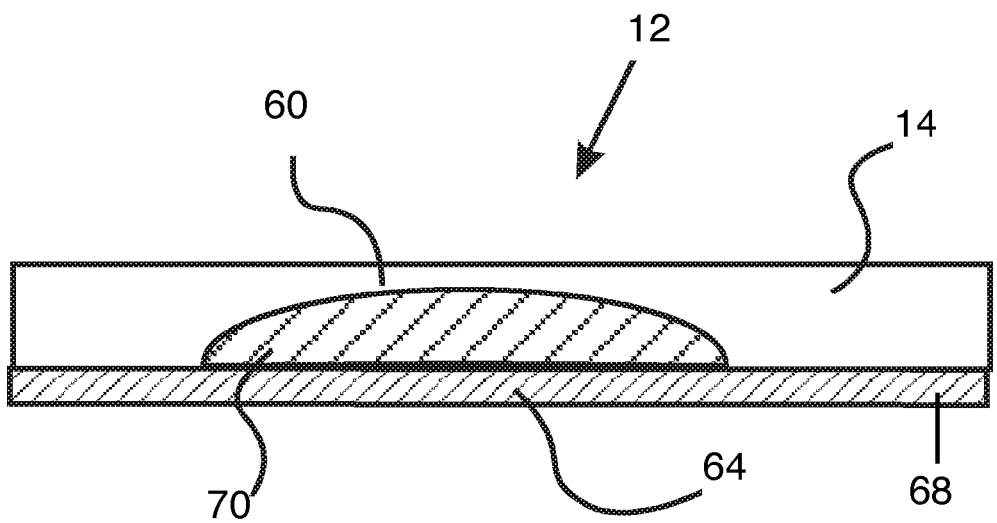

FIG. 3B depicts a laminate adhesive patch 12 comprising a biocompatible material 14, which has an internal reservoir 60 containing bioactive material 70, the inferior surface of which is disposed on and in contact with the superior surface of a permeable biocompatible adhesive layer 68 comprising a fast-setting adhesive 64. The adhesive layer 68 is of such a composition that the bioactive material 70 can permeate through. The remainder of the patch 12 dissolves upon being exposed to water. The bioactive material 70 can be a pharmaceutical.

Figure 4:
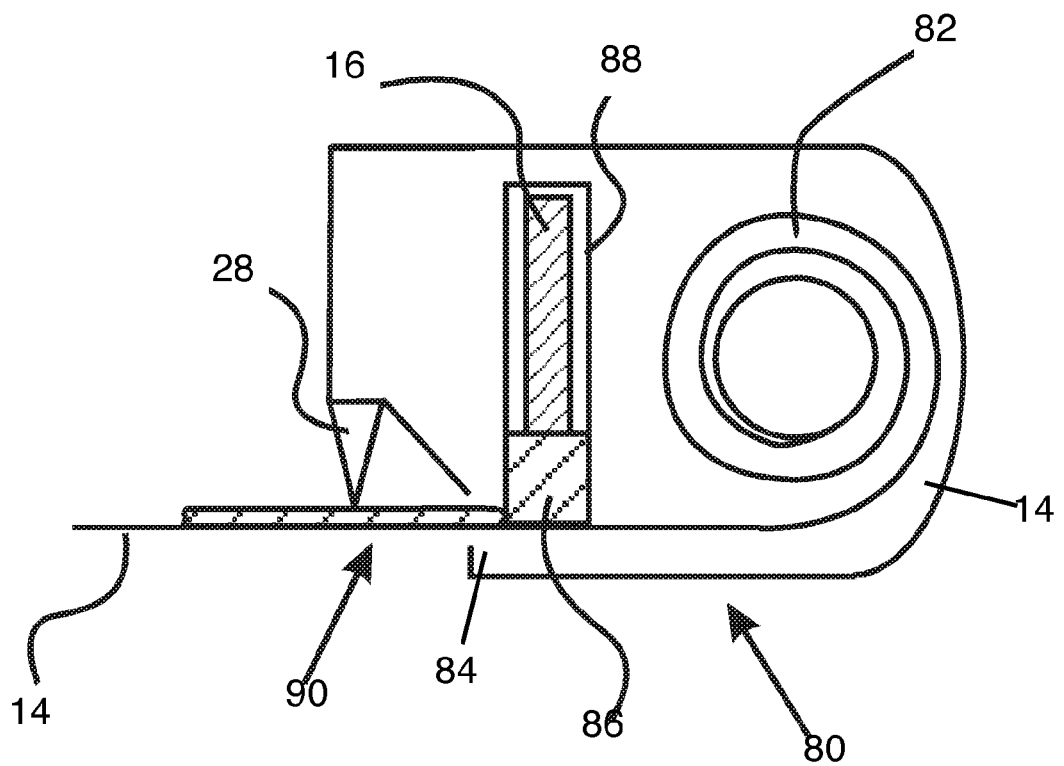
FIG. 4 depicts an adherent tissue patch dispenser.

Again with continued reference to FIG. 1A, FIG. 4 depicts a dispenser 80 comprising a roll 82 of biocompatible material 14 which can be drawn, through manual effort, from the dispenser 80. When the biocompatible material 14 is drawn from the dispenser 80, it contacts brush 84, or other applicator, which is impregnated with the fast-acting adhesive 16. The adhesive 16 coats the biocompatible material 14 as it contacts brush 84, thus forming an adhesive tape 90. A cutter 86 cuts adhesive tape 90 when an appropriate length has been drawn through the dispenser 80.

Optionally, the dispenser 80 may comprise a receptacle 88 to contain the fast-acting adhesive 16 which may polymerize rapidly upon contact with air and/or moisture. Receptacle 88 may be broken open manually, for example, as with a glass ampoule, prior to use of the dispensor 80. Upon breaking the receptacle 88, the adhesive 16 flows into the brush 84. The brush 84 is impregnated with adhesive 16 and can apply the adhesive 16 to the biocompatible material 14.

The following examples are given for the purpose of illustrating various embodiments of the invention and are not meant to limit the present invention in any fashion.

Example 1

Inhibition of Cyanoacrylate Polymerization

A drop of commercial industrial fast-drying cyanoacrylate adhesive was aliquoted onto a small piece of Parafilm-M (Pechiney Plastic Packaging, Chicago Ill.) and onto a teflon cooking pan and left in ambient room conditions. In each case, the cyanoacrylate failed to polymerize. This result was unexpected as the cyanoacrylate is normally considered to combine with moisture in the air and thereby polymerize when in contact with virtually anything, as long as air is present.

Example 2

Flexible Hot-Melt Adhesive

Several pieces of a gummi-type confectionary (Haribo Gummi-Bears) were slowly melted in a glass beaker at approximately 60° C. A sample of approximately 1 ml was placed on a standard glass microscope slide and another slide was then placed in contact with the molten material, overlapping the first slide by about 1 inch and left to dry overnight. The next day, it was impossible to manually separate the two microscope slides, although a small amount of movement was possible due to the elastic nature of the adhesive.

Example 3

Hot-Melt Adhesive Sticks to PTFE

Approximately 20 g of Haribo Gummi-Bears was slowly melted in a glass beaker at approximately 60° C. A mixture of 75% ovalbumin in water was stirred into the confectionary while it was still molten. Samples of the still molten adhesive was placed on teflon (PTFE) cooking pans and pressed down with a teflon plate weighing 1 kg. In one case, a thin film of mineral oil was spread over the PTFE plate prior to application of the adhesive. In another case, a small amount of plastisizer (5% pullulan) was added to the molten mixture prior to application on the PTFE plate.

After allowing to cure overnight, the 1 kg teflon plates were removed and an attempt was made to manually remove the adhesive from the underneath PTFE cooking pan. In all cases, the adhesive adhered very strongly to the plate, which is surprising as only a few materials are known to adhere to teflon. The adhesive with plastisizer stuck best and couldn't be removed, while the adhesive without plastisizer would only be removed by scraping it off with a spatula-like device.

Example 4

Ablation of Stratum Corneum with Cyanoacrylate

A drop of commercial industrial fast-drying cyanoacrylate (Krazy Glue) was aliquoted onto a small piece of clear acetate film. The film was then inverted and placed on the dorsum of a volunteer's forearm. After a period of 2 minutes, a corner of the acetate was raised and the entire piece was rapidly removed from the skin. It was apparent that at least part of the stratum corneum was removed and was left on the acetate sheet, along with any hair that was present on the skin at the treatment site. Application to the ablation site of 200 microliters of 1% lidocaine with epinephrine for 5 minutes and subsequent probing of the site with a 25 G hypodermic needle gave evidence of some degree of anesthesia. The epinephrine caused a blanching of the skin, as measured by a Minolta chromameter. These results are clear evidence of stratum corneum ablation with the cyanoacrylate and film laminate.

Example 5

Biocompatible Films

Several different formulations of thin films were tested for various desirable mechanical properties such as thickness, strength, elasticity and water-solubility: (1) 11% aqueous solution of pullulan; (2) 6% aqueous solution of pullulan with 2.5% aqueous gelatin; (3) 3% aqueous solution of pullulan with approximately 11% glycerol and 3.8% PEG8000 (polyethylene glycerol with a molecular weight of 8000) added; and (4) 6% aqueous solution of pullulan with 0.3% aqueous iota-carageenen. Aliquots of the four test films were applied to a PTFE cooking plate and left to dry overnight. All of the dried samples varied between 0.06 and 0.15 mm in thickness.

Sample 1 was smooth and quite strong, while sample 2 had undesirable bubbles and was more fragile. Sample 3 was strong and much more flexible than sample 1, while sample 4 was also flexible, but not as smooth as the other samples. None of the samples adhered strongly to the PTFE plate. One film with excellent properties as a laminate film was made out of water, pullulan, PEG8000, and glycerol. Other concentrations of these four components were tested which provided superior flexibility, elasticity and uniformity in thickness. Other potentially useful films were made up of pullan (e.g. 5%) and iota-carageenen (e.g. 0.38%). All samples subsequently dissolved well in water, although at differing rates.

Example 6

More Biocompatible Films

Several more formulations of thin films were tested for various desirable mechanical properties: (1) 10% aqueous lambda carageenen-results after drying overnight: elastic, flexible and with high tensile strength; (2) 0.75% aqueous lambda carageenen with 25% glycerol-results after drying overnight: sticks well to PTFE plate, but not to fingers; (3) 0.5% aqueous lambda carageenen with 0.5% PEG8000-results after drying overnight: very uniform, strong and flexible, but slightly retarded dissolving time in water; (4) 5% aqueous pullulan and 0.5% lambda carageenen-results after drying overnight: strong and flexible, but not very elastic, good solubility in water, adheres to moist tissue readily); (5) 10% aqueous hydroxypropyl cellulose-results after drying overnight: very strong and flexible, slightly elastic, vinyl-like; (6) 0.86% aqueous lambda carageenen and 14% glycerol-results after drying overnight: elastic, doesn't adhere to dry tissue readily but adheres readily to moist tissue; (6) 2.5% aqueous hydroxypropyl cellulose, 5% lambda carageenen and 2.5% pullulan-results after drying overnight: strong and flexible, slightly elastic, good solubility in water.

Example 7

Thin Film Adhesive Shields

Several thin films were prepared for the purpose of shielding adhesives. Cyanoacrylate glues were applied to human skin or to wood strips, then covered with thin films prepared from formulations comprised primarily of pullulan and lambda-carageenan. Polysorbate-A was added in low concentrations in some formulations. Thin films were prepared by mixing pullulan (5-10% w/v), lambda-carageen (0.1-0.5% w/v) and polysorbate-A (0-0.1% v/v). In some samples food coloring was added to improve visibility.

Samples (15 ml) were applied to the center of 7 cm diameter plastic rings and the material was allowed to dry overnight, resulting in thin films (approx. 20-50 micron thickness) with good flexibility and solubility characteristics. Upon further evaluation, it was demonstrated that the shields could be applied to the surface of cyanoacrylate glues, as well as other adhesives, and then washed from the surface following curing of the glue, with no apparent alteration of the glue.

Example 8

Thin Film Adhesive Laminates

Multi-layer laminates were prepared for the purpose of shielding adhesives and improving the adherence of the laminate to tissues. In this experiment, the adhesive shield was prepared as in Examples 5-7. Various films then were applied to one another prior to complete drying. In these experiments, films prepared as described in Examples 5 and 6 were allowed to reach 75-95% dryness before layering with the shield material prepared as in example 7. This resulted in laminates with different properties on each side.

The adhesive shield on one side allowed the material to be manipulated freely, while the other side provided for other properties, such as tissue adherence. At times, adhesives were sandwiched between the two films in order to provide a complete system. With this type of laminate, an adhesive material may be applied to the surface of moist membranous wounds, such that the tissue adhering layer immediately sticks to the tissue, thereby immediately localizing the adhesive at the wound site, while a protective layer shields the applicator from the adhesive One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for delivering a bioactive agent to one or more tissues, comprising the step of:
    positioning a laminate device in contact with the one or more tissues, said laminate device comprising a continuous layer of cyanoacrylate adhesive and one or more layers of a biocompatible non-adherent substance disposed in protective and covering relationship to the cyanoacrylate adhesive;
    wherein one or more of the layers of the laminate device comprises the bioactive agent thereby delivering said bioactive agent to the one or more tissues.

2. The method of claim 1, wherein positioning the laminate device comprises:
    applying the cyanoacrylate comprising the device as a continuous layer onto the tissue(s); and
    covering, in protective relationship, the cyanoacrylate layer with one or more layers of the biocompatible non-adherent substance comprising the laminate device.

3. The method of claim 2, wherein at least one of the layers of the biocompatible non-adherent substance is disposed on one or both surfaces of the continuous cyanoacrylate adhesive layer.

4. The method of claim 1, further comprising the step of: activating the cyanoacrylate adhesive after positioning the laminate device.

5. The method of claim 4, wherein the laminate device further comprises one or more removable layers disposed in contact with the cyanoacrylate adhesive, with one or more layers of the biocompatible non-adherent substance or a combination thereof, said method further comprising the step of:
removing one or more of the removable layers, wherein if the one or more removable layers are disposed only on a surface of the continuous cyanoacrylate adhesive layer, said one or more removable layers are removed prior to positioning the laminate device or if the one or more removable layers are disposed on one or more layers of the biocompatible non-adherent substance comprising the laminate device, said one or more removable layers are removed after activating the cyanoacrylate adhesive or a combination thereof;
wherein the biocompatible non-adherent substance and the one or more removable layers protects the continuous cyanoacrylate adhesive layer from unintentional bonding to the one or more tissues.

6. The method of claim 5, wherein the one or more removable layers are disposed between the cyanoacrylate adhesive and the biocompatible non-adherent substance or are disposed in covering relationship to an outer layer of the biocompatible non-adherent substance.

7. The method of claim 6, wherein the one or more removable layers independently comprises a polymer, Polytetrafluorethylene (PTFE) or a cellulose impregnated with a lecithin, polyethylene glycol, a wax or other lipid.

8. The method of claim 1, further comprising the step of: dissolving the biocompatible non-adherable protective substance upon contact with water or other fluid.

9. The method of claim 1, wherein the one or more layers of the biocompatible non-adherent substance comprises pullalan or other hydrocolloid.

10. The method of claim 1, wherein one or more layers of the biocompatible non-adherent substance further comprises an emulsifying agent, a solubilizing agent, a wetting agent, a taste modifying agent, a plasticizer, a bioactive agent, a water soluble inert filler, a preservative, a buffering agent, a coloring agent, a stabilizer, or a combination thereof.

11. The method of claim 1, wherein the bioactive agent is the cyanoacrylate adhesive comprising the layer in contact with the tissue(s), the method further comprising setting the cyanoacrylate adhesive to join the tissue(s).

12. The method of claim 1, wherein the bioactive agent is a pharmaceutical contained within a rupturable reservoir within one or more layer(s) disposed in contact with the continuous cyanoacrylate adhesive layer and between the adhesive layer and the tissue(s), the method further comprising rupturing the reservoir prior to diffusing said pharmaceutical and setting the cyanoacrylate adhesive.

13. The method of claim 1, wherein the tissue is skin.

14. The method of claim 1, wherein the laminate device comprises a patch.

15. A method of preventing unintentional bonding of a cyanoacrylate adhesive during application thereof to one or more tissues, comprising:
positioning onto the one or more tissues a laminate device having:
a continuous layer of cyanoacrylate adhesive;
at least one layer of a biocompatible non-adherent substance disposed in protective and covering relationship to the cyanoacrylate adhesive;
and one or more removable layer disposed in contact with the cyanoacrylate adhesive, with one or more layers of the biocompatible non-adherent substance or a combination thereof;
wherein the continuous cyanoacrylate adhesive layer is in contact with the one or more tissues;
activating the cyanoacrylate adhesive; and
removing one or more of the removable layers, wherein if the one or more removable layers are disposed only on a surface of the continuous cyanoacrylate adhesive layer, said one or more removable layers are removed prior to positioning the laminate device or if the one or more removable layers are disposed on one or more layers of the biocompatible non-adherent substance, said one or more removable layers are removed after activating the cyanoacrylate adhesive or a combination thereof;
wherein the biocompatible non-adherent substance and the one or more removable layers protect the continuous cyanoacrylate adhesive layer thereby preventing unintentional bonding of the cyanoacrylate adhesive.

16. The method of claim 15, wherein positioning the laminate device comprises:
applying the cyanoacrylate comprising the device as a continuous layer onto one or more tissues; and
covering, in protective relationship, the cyanoacrylate layer with the one or more removable layers or with the one or more layers of the biocompatible non-adherent substance having the one or more removable layers disposed thereon.

17. The method of claim 15, further comprising: setting the cyanoacrylate adhesive to join the one or more tissues.

18. The method of claim 15, wherein the removable layer comprises a polymer, Polytetrafluorethylene (PTFE) or a cellulose impregnated with a lecithin, polyethylene glycol, a wax or other lipid.

19. The method of claim 15, wherein one or more layers of the biocompatible non-adherent substance further comprises an emulsifying agent, a solubilizing agent, a wetting agent, a taste modifying agent, a plasticizer, a bioactive agent, a water soluble inert filler, a preservative, a buffering agent, a coloring agent, a stabilizer, or a combination thereof.

20. The method of claim 15, wherein one or more layers of said biocompatible non-adherent substance further comprises a pharmaceutical or a pharmaceutical contained within a rupturable reservoir within said one or more layers.

21. The method of claim 15, wherein the one or more layers of the biocompatible non-adherent substance is disposed on one or both surfaces of the continuous cyanoacrylate adhesive layer.

22. The method of claim 15, wherein the biocompatible non-adherable protective substance is dissolvable upon contact with water or other fluid.

23. The method of claim 15, wherein one or more layers of the biocompatible non-adherent substance comprises pullalan or other hydrocolloid.

24. The method of claim 15, wherein the laminate device comprises a patch.

25. The method of claim 15, wherein the tissue is skin.

* * * * *